United States Patent [19]
Beaty et al.

[11] Patent Number: 6,152,737
[45] Date of Patent: *Nov. 28, 2000

[54] SUPPORT POST FOR USE IN DENTAL IMPLANT SYSTEM

[75] Inventors: Keith D. Beaty, West Palm Beach; Richard J. Lazzara, Lake Worth, both of Fla.

[73] Assignee: Implant Innovations, Inc., Palm Beach Gardens, Fla.

[*] Notice: This patent is subject to a terminal disclaimer.

[21] Appl. No.: 09/274,181

[22] Filed: Mar. 23, 1999

Related U.S. Application Data

[63] Continuation of application No. 08/920,943, Aug. 29, 1997, Pat. No. 5,947,732, which is a continuation of application No. 08/674,658, Jul. 2, 1996, Pat. No. 5,685,714, which is a continuation of application No. 08/260,775, Jun. 16, 1994, abandoned.

[51] Int. Cl.[7] .................................................. A61C 8/00
[52] U.S. Cl. ............................................ 433/172; 433/173
[58] Field of Search .................................. 433/172, 173, 433/174

[56] References Cited

U.S. PATENT DOCUMENTS

| | | | |
|---|---|---|---|
| 2,721,387 | 10/1955 | Ashuckian | 32/10 |
| 4,259,072 | 3/1981 | Hirabayashi et al. | 433/173 |
| 4,560,353 | 12/1985 | Schulte et al. | 433/173 |
| 4,575,340 | 3/1986 | Lustig | 433/173 |
| 4,746,293 | 5/1988 | Lundgren et al. | 433/173 |
| 4,758,161 | 7/1988 | Niznick | 433/173 |
| 4,824,372 | 4/1989 | Jörnéus et al. | 433/174 |
| 4,846,683 | 7/1989 | Lazzara et al. | 433/173 |
| 4,850,870 | 7/1989 | Lazzara et al. | 433/174 |
| 4,850,873 | 7/1989 | Lazzara et al. | 433/220 |
| 4,854,872 | 8/1989 | Detsch | 433/173 |
| 4,856,994 | 8/1989 | Lazzara et al. | 433/173 |
| 4,872,839 | 10/1989 | Brajnovic | 433/173 |

(List continued on next page.)

FOREIGN PATENT DOCUMENTS

| | | |
|---|---|---|
| 0 320 024 A1 | 6/1989 | European Pat. Off. . |
| 0 477 644 A1 | 4/1992 | European Pat. Off. . |
| 0 657 146 A1 | 6/1995 | European Pat. Off. . |
| 21 57 139 | 5/1972 | Germany . |
| 27 17 506 | 5/1978 | Germany . |
| 32 24 112 A1 | 2/1984 | Germany . |
| 38 25 601 A1 | 3/1989 | Germany . |
| 41 27 839 A1 | 3/1992 | Germany . |
| 1570720 A1 | 6/1990 | U.S.S.R. . |
| 2 213 065 | 8/1989 | United Kingdom . |

OTHER PUBLICATIONS

Perri, George, DDS et al., Single Tooth Implants, CDA Journal, vol. 17, No. 3, Mar. 1989.

Dental Imaging Associates, Inc., et al., *The DIA Anatomic Abutment System*™, pp. 1–10, Oct. 1991.

Lewis, S.G., et al., Single Tooth Implant Supported Restorations, The International Journal of Oral & Maxillofacial Implants, vol. 3, No. 1, pp. 25–30, 1988.

Lewis, S., et al., The "UCLA" Abutment, The International Journal of Oral & Maxillofacial Implants, vol. 3, No. 3, pp. 183–189, 1988.

Zirconium Diboride/Zirconium Carbide/Zirconium Composites for orthopedic applications (no date).

V. A. Ravi, T. D. Claar, B. Berelsman and J. Higgins (no date).

*Primary Examiner*—John J. Wilson
*Attorney, Agent, or Firm*—Jenkens & Gilchrist

[57] ABSTRACT

A support post for use with a dental implant for supporting a prosthesis thereon is disclosed. The support post includes an implant-contacting region and a supragingival core section which extends from the trans-tissue region for supporting a prosthesis. An interface member is secured to the post at the bottom of the implant-contacting region for abutment between the implant-contacting region and an implant to which the post is to be secured. The interface member has material properties different from those from which the post is made and compatible with those of the implant. Typically the support post is made of ceramic material while the insert is made of titanium having hardness properties no greater than that of the implant with which it is used.

30 Claims, 8 Drawing Sheets

U.S. PATENT DOCUMENTS

| | | | |
|---|---|---|---|
| 4,904,187 | 2/1990 | Zingheim | 433/173 |
| 4,955,811 | 9/1990 | Lazzara et al. | 433/173 |
| 4,978,640 | 12/1990 | Kelly | 501/32 |
| 4,988,297 | 1/1991 | Lazzara et al. | 433/173 |
| 4,988,298 | 1/1991 | Lazzara et al. | 433/173 |
| 5,000,686 | 3/1991 | Lazzara et al. | 433/174 |
| 5,006,069 | 4/1991 | Lazzara et al. | 433/173 |
| 5,015,186 | 5/1991 | Detsch | 433/173 |
| 5,022,860 | 6/1991 | Lazzara et al. | 433/174 |
| 5,030,096 | 7/1991 | Hurson et al. | 433/173 |
| 5,035,619 | 7/1991 | Daftary | 433/173 |
| 5,040,982 | 8/1991 | Stefan-Dogar | 433/173 |
| 5,040,983 | 8/1991 | Binon | 433/173 |
| 5,064,373 | 11/1991 | Staubli et al. | 433/173 |
| 5,071,345 | 12/1991 | Rosen | 433/17 |
| 5,071,351 | 12/1991 | Green, Jr. et al. | 433/173 |
| 5,073,111 | 12/1991 | Daftary | 433/173 |
| 5,082,442 | 1/1992 | Rosen | 433/17 |
| 5,087,200 | 2/1992 | Brajnovic et al. | 433/173 |
| 5,100,323 | 3/1992 | Friedman et al. | 433/173 |
| 5,105,690 | 4/1992 | Lazzara et al. | 81/436 |
| 5,106,300 | 4/1992 | Voitik | 433/173 |
| 5,125,839 | 6/1992 | Ingber et al. | 433/169 |
| 5,135,395 | 8/1992 | Marlin | 433/174 |
| 5,145,371 | 9/1992 | Jörnéus | 433/173 |
| 5,145,372 | 9/1992 | Daftary et al. | 433/173 |
| 5,152,687 | 10/1992 | Amino | 433/173 |
| 5,154,612 | 10/1992 | Carlsson et al. | 433/173 |
| 5,169,309 | 12/1992 | Staubli et al. | 433/173 |
| 5,188,800 | 2/1993 | Green, Jr. et al. | 422/23 |
| 5,209,659 | 5/1993 | Friedman et al. | 433/173 |
| 5,209,666 | 5/1993 | Balfour et al. | 433/173 |
| 5,213,502 | 5/1993 | Daftary | 433/172 |
| 5,246,370 | 9/1993 | Coatoam | 433/173 |
| 5,281,140 | 1/1994 | Niznick | 433/172 |
| 5,282,746 | 2/1994 | Sellers et al. | 433/172 |
| 5,292,252 | 3/1994 | Nickerson et al. | 433/173 |
| 5,297,963 | 3/1994 | Daftary | 433/172 |
| 5,316,476 | 5/1994 | Krauser | 433/173 |
| 5,334,024 | 8/1994 | Niznick | 433/173 |
| 5,336,090 | 8/1994 | Wilson, Jr. et al. | 433/173 |
| 5,338,196 | 8/1994 | Beaty et al. | 433/172 |
| 5,368,483 | 11/1994 | Sutter et al. | 433/173 |
| 5,419,702 | 5/1995 | Beaty et al. | 433/214 |
| 5,431,567 | 7/1995 | Daftary | 433/172 |
| 5,447,435 | 9/1995 | Brodbeck | 433/172 |
| 5,476,383 | 12/1995 | Beaty et al. | 433/214 |
| 5,492,471 | 2/1996 | Singer | 433/172 |
| 5,685,714 | 11/1997 | Beaty et al. | 433/173 |

SUPPORT POST FOR USE IN DENTAL IMPLANT SYSTEM

RELATED APPLICATIONS

This application is a continuation of U.S. patent application No. 08/920,943, filed Aug. 29, 1997, now U.S. Pat. No. 5,947,732; which is a continuation application of U.S. patent application No. 08/674,658, filed Jul. 2, 1996, and issued as U.S. Pat. No. 5,685,714 on Nov. 11, 1997; which is a file wrapper continuation of U.S. application No. 08/260,775, filed Jun. 16, 1994, now abandoned.

BACKGROUND OF THE INVENTION

This invention relates to a support post for use with a bone-embedded dental implant. Specifically, the invention relates to a support post which is made of a material having different properties from the material of the implant with which it is to be used, and which includes an interface made of material compatible in hardness, with the material of the implant with which it is to be used and which is radiopaque. Such support posts support a prosthesis superstructure such as an artificial tooth.

Surgical techniques for support of dental prostheses by means of metallic bone-embedded artificial root fixtures are well known. According to one prior art technique, a titanium bone-embedded implant fixture is interfaced with a metallic to abutment post, on which the superstructure is supported. The post has an internally shouldered access bore through which a screw fastener is inserted to actually hold the implant and the post assembled. A number of problems and restrictions are presented however in the attachment of and retention of the superstructures to such abutment posts.

Specifically, the typical superstructures for use with such posts are made of porcelain. The use of a titanium post generally results in a dark, central rod-like shadow, particularly when exposed to high-brightness light, which makes the prosthesis somewhat unattractive and able to be distinguished from a natural tooth. Further, since the materials are different, there are sometimes presented problems with securing of the prosthesis to the support post.

One attempt to solve the attractiveness and securing problems has involved making a support post made entirely of ceramic material, specifically, aluminum oxide. This approach allows direct surface bonding by interaction of a porcelain coping and/or prosthesis to the support post resulting in a secure and almost seamless bond between the prosthetic structure and the support post. While presenting an alternative attraction to the use of a titanium support post, the proposed solution presents a number of previously unanticipated problems.

Ceramic materials generally have a much greater hardness than titanium. When such a support post is used, inevitable rocking of the support post due to, for example, chewing action, causes a high-stress interaction between the metal implant and the ceramic material of the post. Since ceramic is of greater hardness than the titanium implant, it can and does cause damage to the implant. If sufficient damage is caused, eventual surgical intervention is required to remove and replace the titanium implant. In addition, ceramic material is typically not radiopaque. Thus, when examining the juncture between the support post and the titanium implant through conventional dental x-ray imaging, the interface between the two elements is not readily viewable and thus adequate x-ray examination cannot be conducted.

These and other problems relating to the use of an all-ceramic support post are avoided by the support post of the invention as described hereafter.

SUMMARY OF THE INVENTION

In accordance with one aspect of the invention, there is provided an improved support post for use with a dental implant for supporting a prosthesis thereon. The support post may include an implant-contacting region such as trans-issue region integral with the post. A supragingival core section extends from the implant or from the implant-contacting region, such as a trans-tissue region, for supporting a prosthesis thereon. An interface member is secured to the post at least at the juncture between the post or the trans-tissue region, if present, for abutment between the post, or the trans-tissue region, and an implant to which the post is to be secured. The interface member has material properties different from those from which the support post is made.

In a more specific aspect, the support post is made of a material having greater hardness than the implant with which it is to be used and the interface member is made of a material having a hardness no greater than the implant with which it is to be used. Preferably, the interface member is opaque to x-rays. Yet more preferably, the support post is of ceramic material and the interface member is of the same material as the implant with which it is to be used, e.g., titanium.

In a yet still more specific aspect, the support post is hollow with a passageway extending therethrough and the interface member is an insert which is press-fitted in the passageway. The insert preferably extends completely along the bottom surface of the support post to prevent contact between the harder material of the support post and an implant with which it is to be used. Optionally, the insert further includes an upper portion extending coaxially within the passageway in contact with the inner walls of the support post defining the passageway. The support post includes a shoulder portion extending centrally from the inner walls to provide a shoulder for the head of the screw for use in securing the support post to an implant.

BRIEF DESCRIPTION OF THE DRAWINGS

Having generally described the invention, the same will become better understood from the following detailed discussion made with reference to the attached drawings wherein.

DETAILED DISCUSSION

Figure 1:
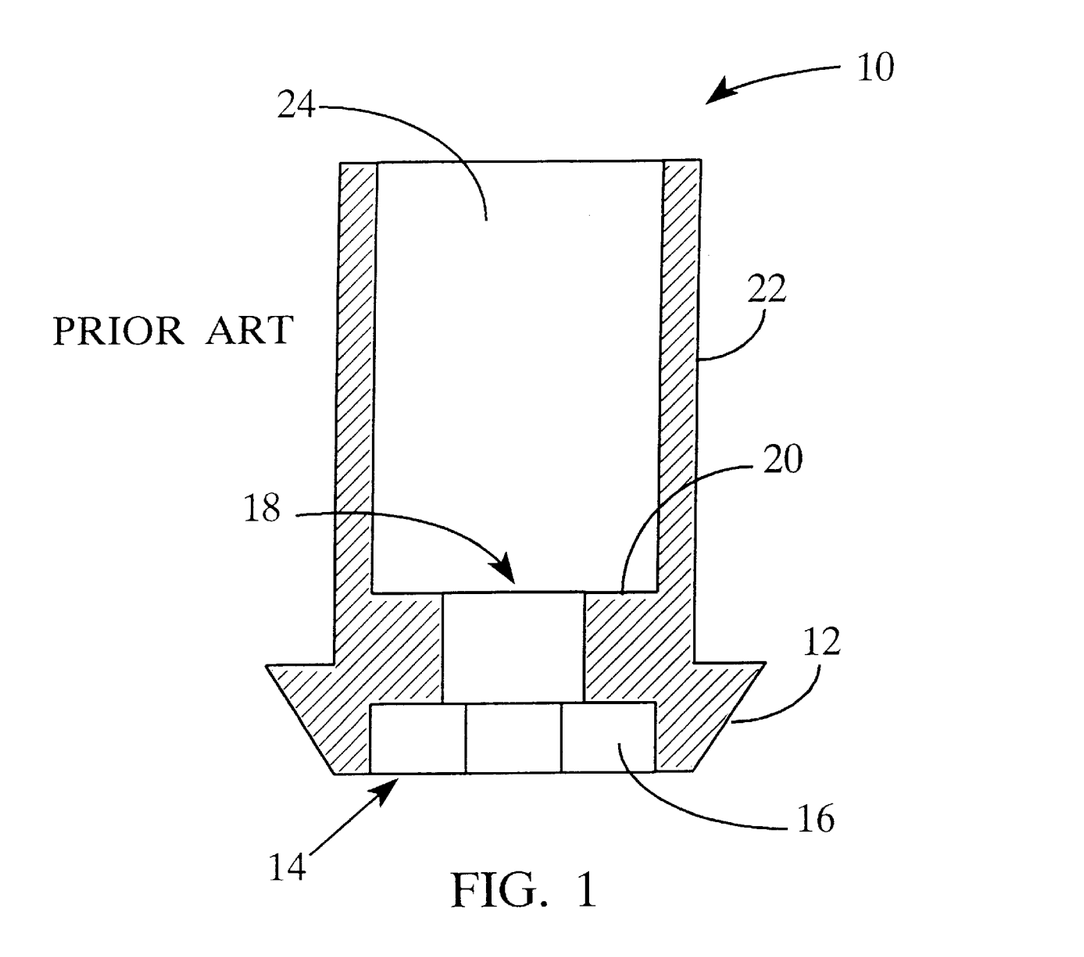
FIG. 1 is a side cross-sectional view of a typical prior art support post.

Referring now to the drawings in detail, FIG. 1 illustrates generally as element 10 a support post in accordance with the prior art. The support post 10 includes an opening 14 at the bottom thereof extending into a passageway 24 which extends upwardly to an open top. The passageway 24 includes at the bottom a shaped region 16, for example, having a multiple flat sides in a generally circular arrangement to prevent rotation of the support post 10 when in abutment and attached to an implant having a corresponding shaped upper member which fits into the shaped region 16. The passageway 24 narrows through a narrower portion 18 with shoulder regions 20 providing a shoulder for the head of a screw which is used to secure the support post 10 to a dental implant. Transgingival region 12 provides a region which is, when attached to an implant, surrounded by the gingival tissue of a patient.

An upper-elongated portion 22 of the support post is shaped for having a prosthesis, optionally with a coping, secured thereto by any one of a number of different means.

In accordance with the prior art, in one aspect the prior art the support post is made of titanium which includes all of the disadvantages heretofore discussed with respect to securing a prosthesis thereto and with respect to the unattractive appearance given to the prosthesis by virtue of the dark shadow left by the elongated portion 22 in the center of the prosthesis. In an alternative configuration of the prior art, the support post 10 of FIG. 1 can be made of all ceramic material such as aluminum oxide, as shown. However, as discussed with reference to such a support post, the ceramic material is of greater hardness than the implants with which it is to be used, and can damage the implant requiring later surgical intervention due to rocking motion of the support post 10 on the implant fixture. Further, ceramic is x-ray radiation transparent thereby not permitting adequate x-ray examination of the interface between the bottom of the support post 10 and the titanium implant with which it is used when secured to an implant in a patient's mouth.

Figure 2:
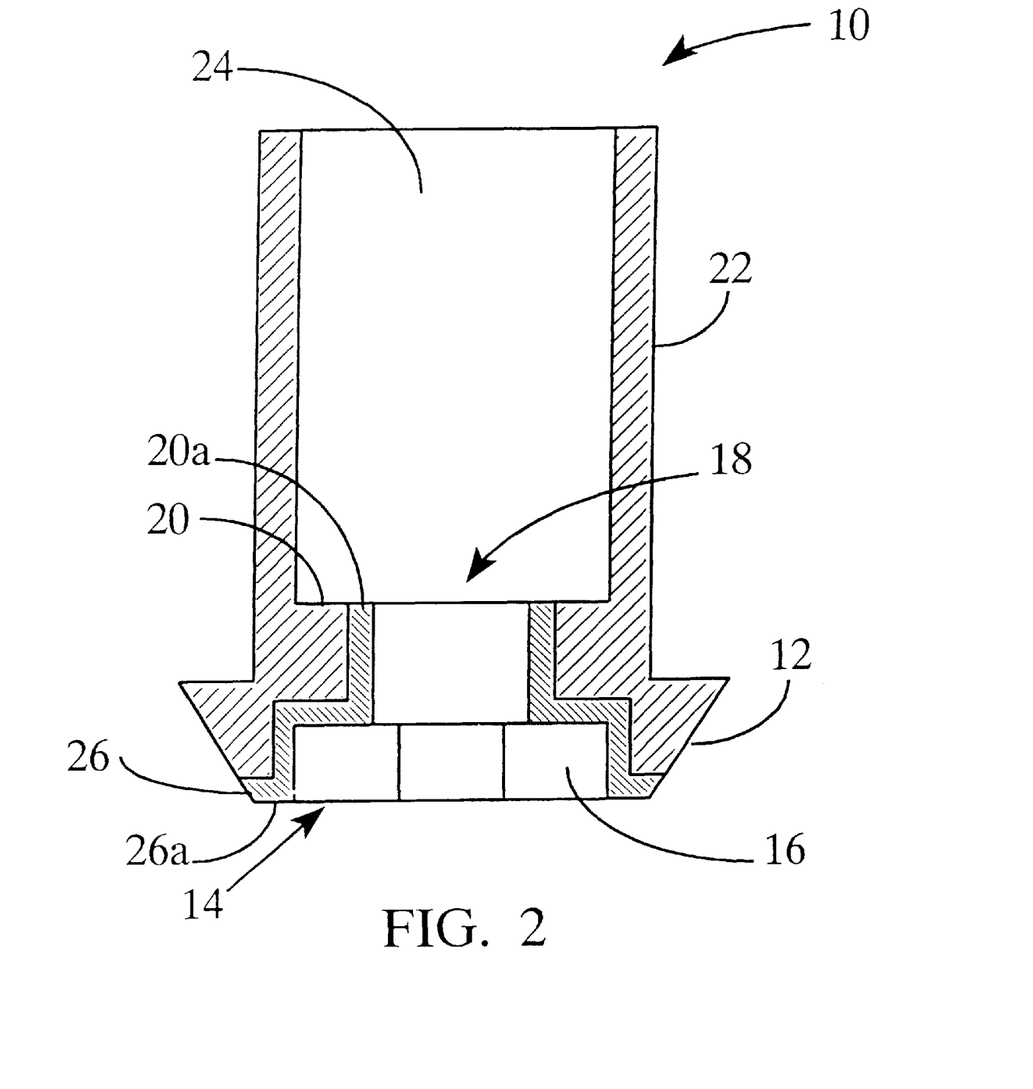
FIG. 2 is a view as in FIG. I showing a support post with a modification including an interface member in accordance with the invention.
Figure 3:
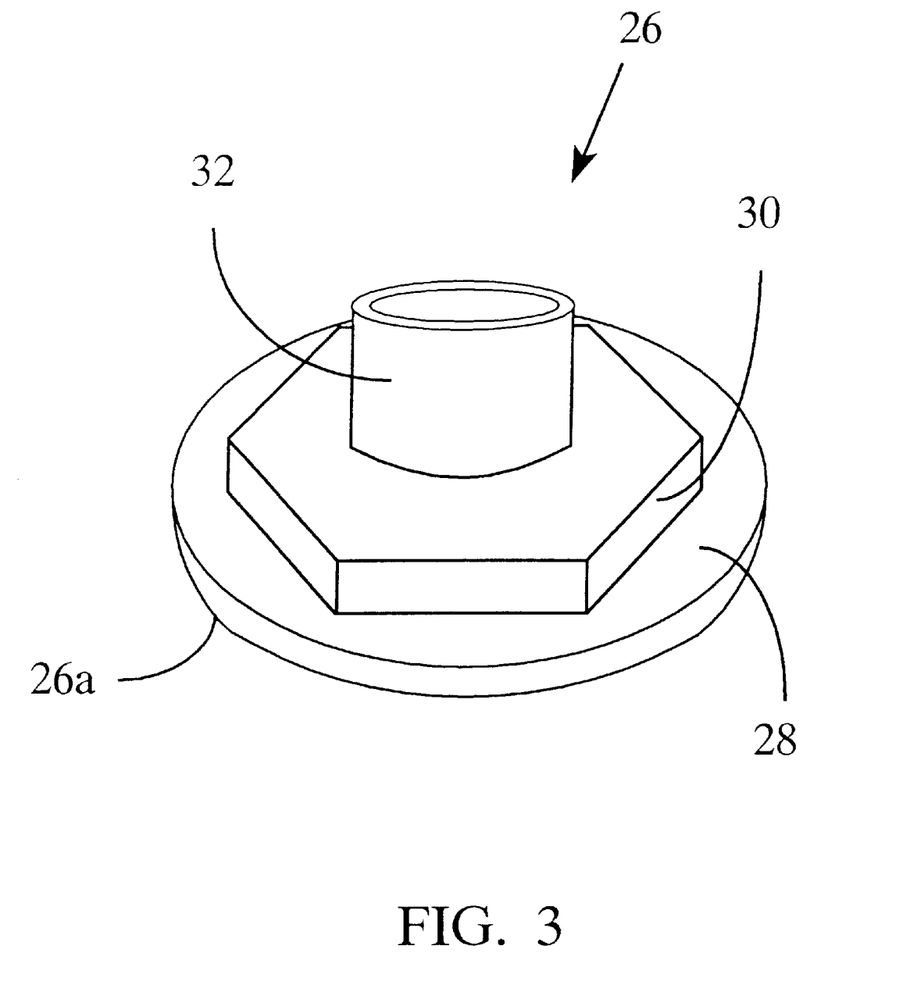
FIG. 3 is a perspective view of one embodiment of the interface member employed in connection with the support post in accordance with the invention.

FIG. 2 shows one embodiment of the invention which employs the ceramic structure shown in FIG. 1, except that an insert 26 is provided to create an interface between the support post 10 and the implant with which it is used to prevent direct contact between the ceramic material of the support post and the dental implant. Specifically, as shown in FIG. 2, and more clearly in FIG. 3, the insert 26 includes a wide-bottom portion 28 having a lower surface 26a which is coextensive with the bottom surface of support post 10. An upwardly extending narrower-shaped region 30 corresponds to shaped region 16 of the passageway 24 of the support post 10, and fits therein in a non-rotational manner, with the inner surface of raised portion 30 including corresponding flat-shaped portions for non-rotational engagement with the appropriate portion of the implant with which it is used. A narrower tubular section 32 fits into narrower passageway 18 and the top edge of the tubular section 32 defines an optional additional shoulder portion 20a for abutment with the head of a screw used to hold the support post 10 attached to an implant.

Figure 4:
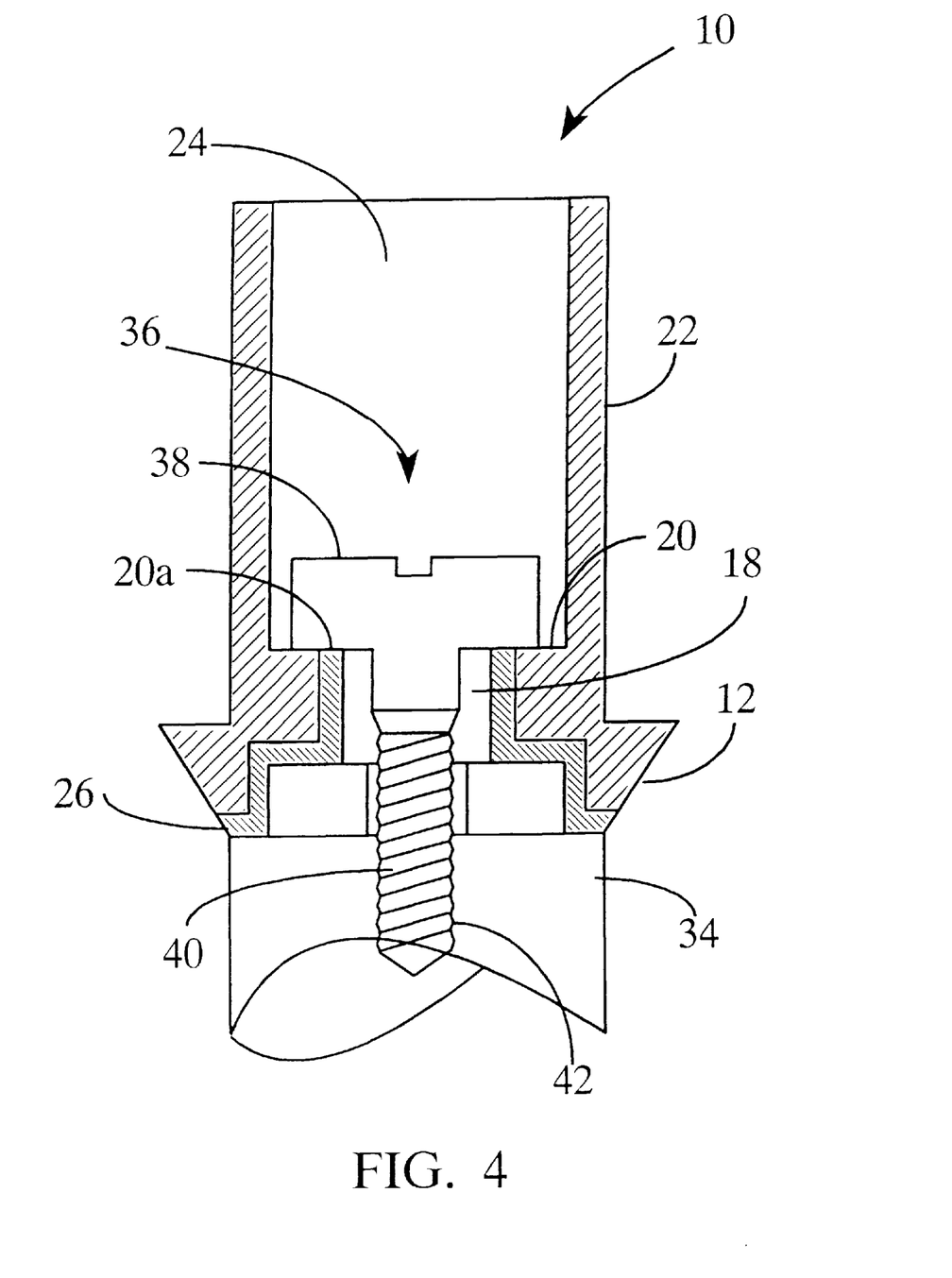
FIG. 4 is a side-cross sectional view showing a typical arrangement of one embodiment of the support post of the invention with the interface member shown assembled to a dental implant in a typical construction.

Such an arrangement of this embodiment of the support post 10 is shown in assembled form with an implant 34 in FIG. 4. Specifically, the implant 34, typically made of titanium or titanium alloy, includes a threaded bore 42 for having a screw received therein. The support post 10 is placed in abutment with implant 32 through interface member 26 and is held secured to the implant 34 by means of a screw 36 having a head 38 which rests against shoulders 20/20a with the threaded portion 40 of the screw in threaded engagement with threaded receiving bore 42 of the implant.

Figure 5:
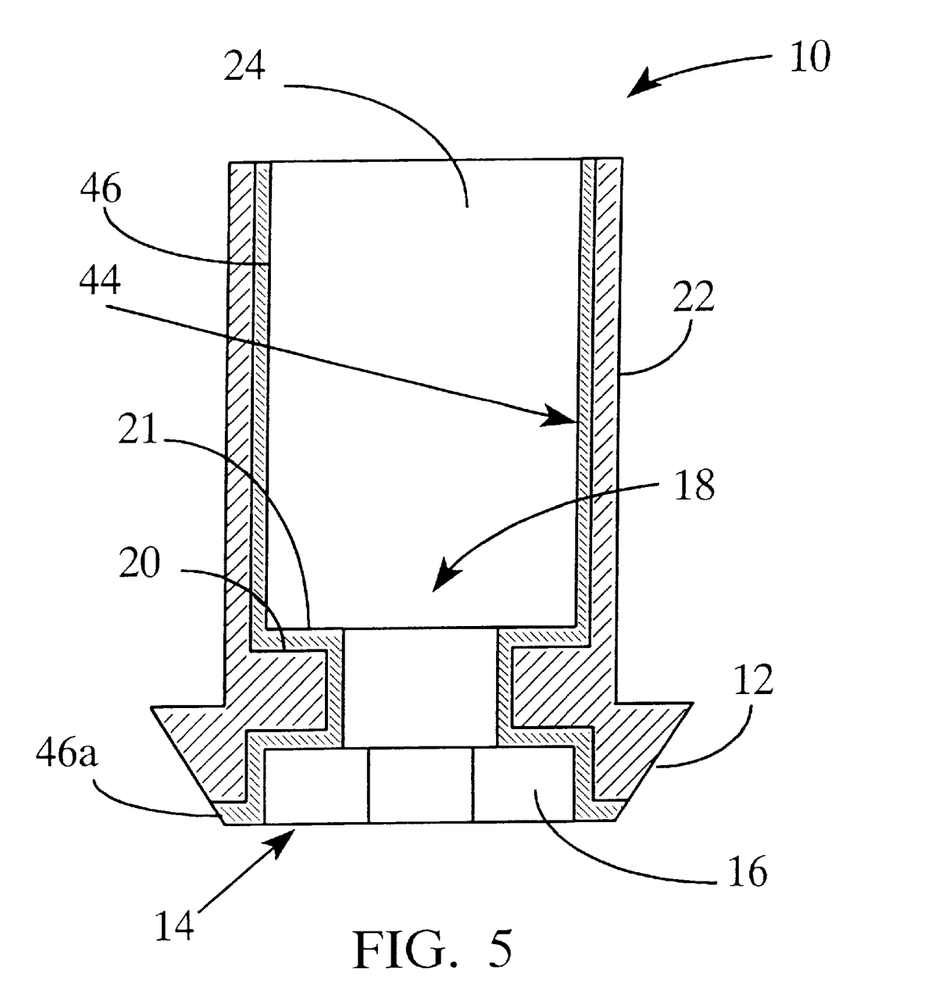
FIG. 5 is a view similar to FIG. 2 but showing a second embodiment of the support posts with an alternative structure for the interface member in accordance with the invention.
Figure 6:
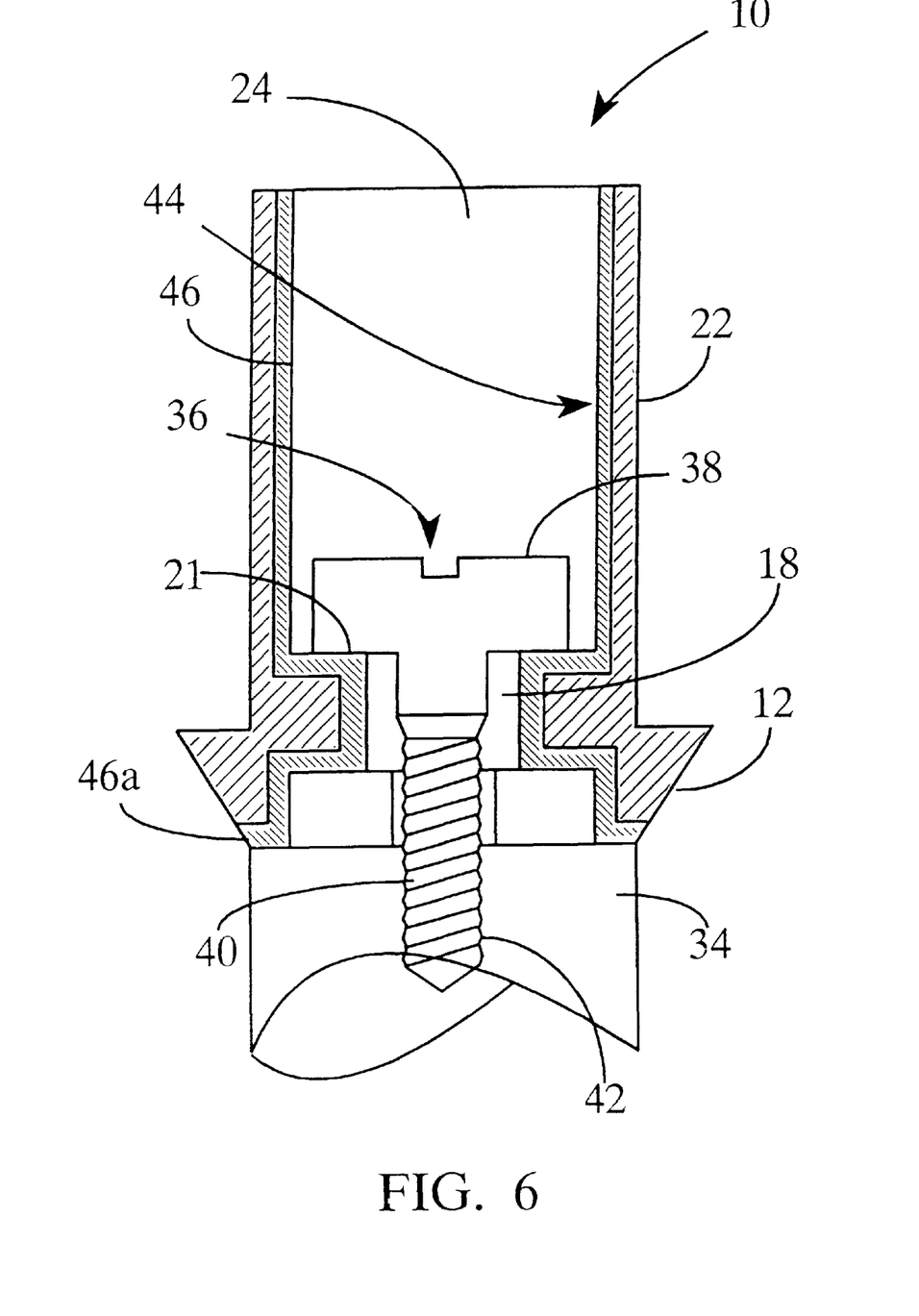
FIG. 6 is a view as in FIG. 4 showing the support post of FIG. 5 in an assembled configuration with a dental implant.

In an alternative configuration shown in FIG. 5, the insert can be an insert 44 which has a portion 46 coextensive with the inner passageway of the support post 10. In this embodiment, shoulder 20 of the support post 10 serves to support a shoulder portion 21 of the insert 44 which serves to support the head 38 of screw 36 as shown in FIG. 6. A lower surface 46a extends along the bottom of the support post 10 in a manner similar to that of lower surface 26a of the embodiment of FIG. 2.

While the insert 26/44 has been described as being made preferably of titanium or titanium alloy, it should be noted that any other medically compatible material having a hardness no greater than the hardness of the material of which the implant 34 is made can be used. The only requirement is that the material for the insert 26/44 also be radiopaque, i.e., opaque to x-rays, so that the interface between the support post 10 and the implant 34 can be medically examined, for example, through the use of conventional x-rays. The insert 26, for example, in the embodiment of FIG. 2, can be manufactured to such high tolerances in the case when titanium is used, that it can be merely press fit in a conventional manner into the support post 10. Alternatively, such other securing means such as conventional cement can be used to secure the insert therein.

Figure 7:
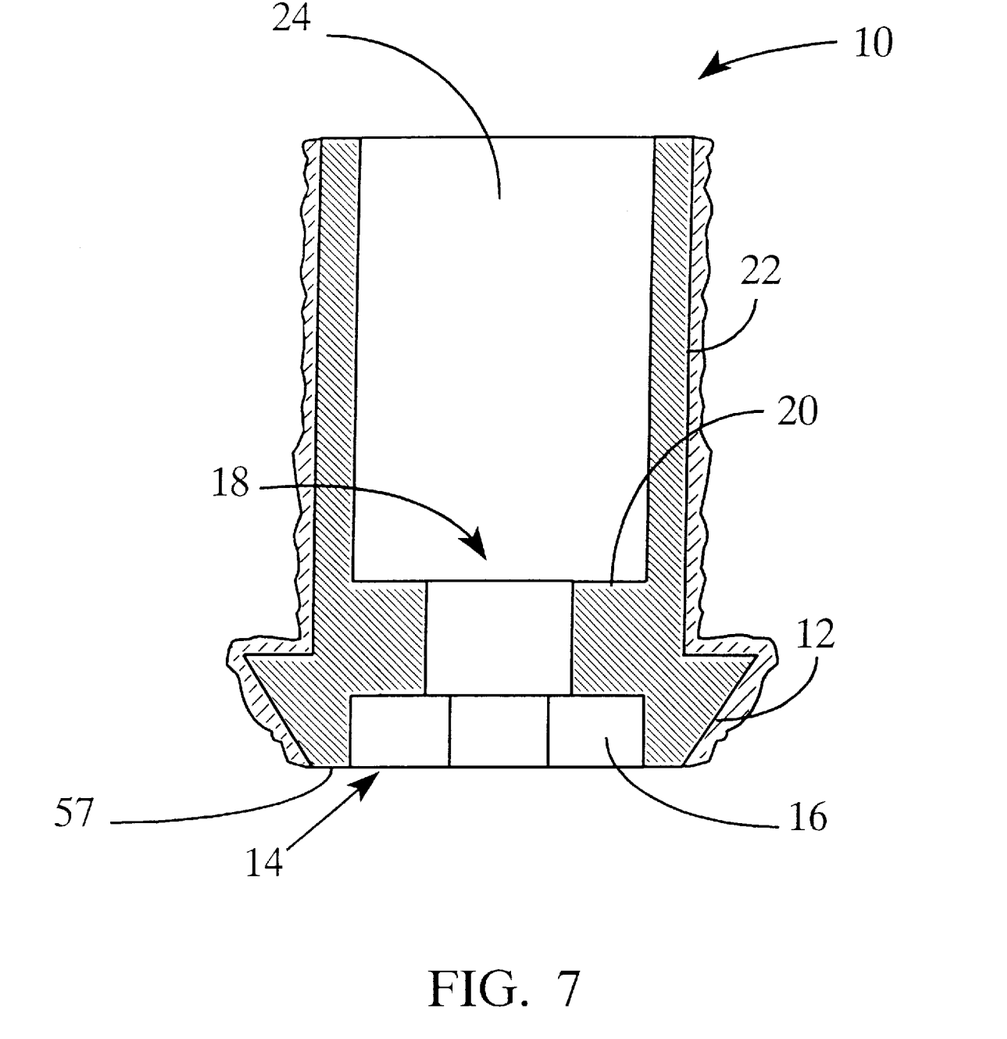
FIG. 7 is a view as FIG. 5 showing an alternative structure of a support post made of a metal such as titanium having a surface of flame sprayed ceramic on the metal post.

FIG. 7 illustrates yet another embodiment of the support post 10. In this case, the entire post 10 is made of a metal such as titanium or titanium alloy. A layer of ceramic material 55 has been flame sprayed in a conventional manner to adhere onto the surface of the metal support post 10. A bottom surface 57 of the support post 10 ensures abutment of metal to metal of comparable hardness between the support post 10 and an implant against which it abuts.

Figure 8:
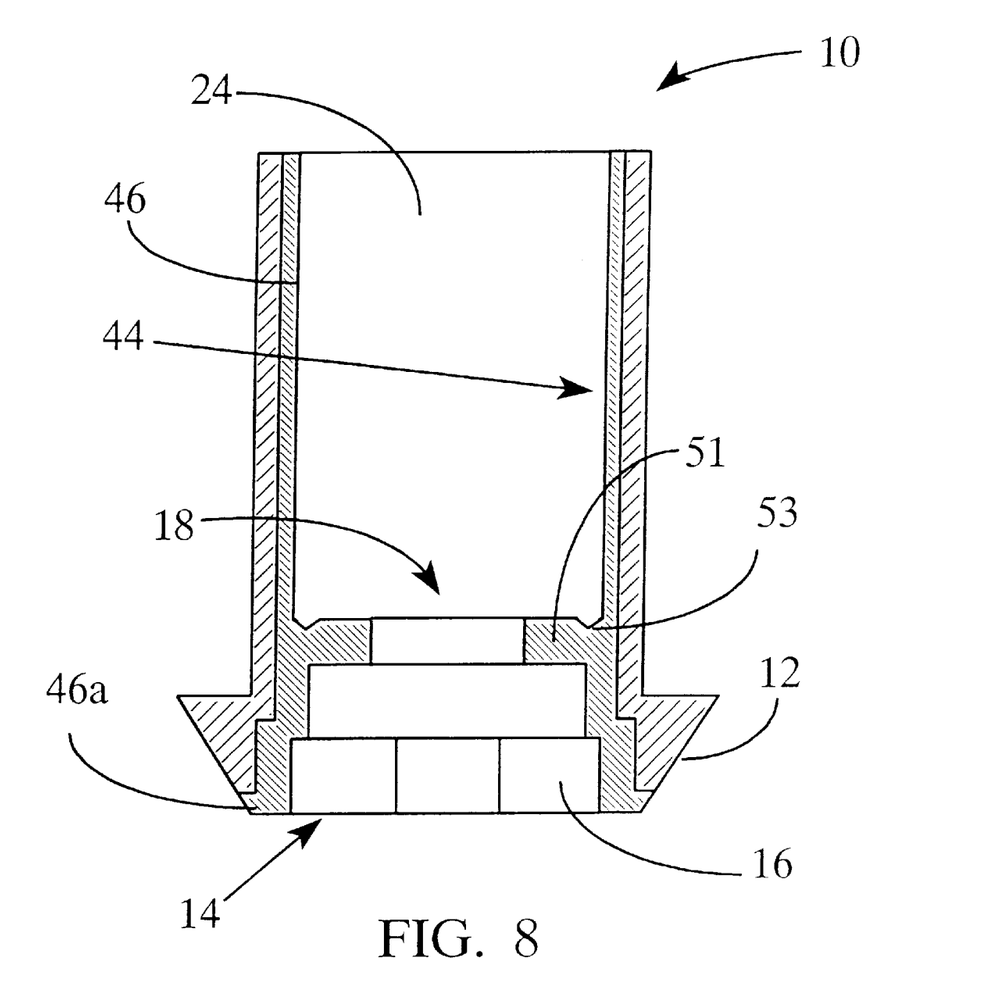
FIG. 8 is a view as in FIG. 5 showing an alternative breakaway arrangement for the screw head avoiding excessive stress from being applied by the support post onto an implant.

FIG. 8 illustrates yet another embodiment of the support post 10 similar to that of FIGS. 5 and 6. In this embodiment a breakaway screw head abutment 51 is provided to ensure that excessive forces are not applied to an implant. The depth of notch 53 is selected in accordance with the maximum force allowed to be applied to the implant. The abutment 51 also ensures that there is no over tightening of the post 10 onto its corresponding implant.

As can be appreciated, the various features of the different embodiments can be combined or interchanged as readily apparent to those of ordinary skill in the art. For instance, the breakaway abutments 51 of FIG. 8 can easily be adapted for use in the embodiment of FIG. 6, in a manner which will be apparent to those of ordinary skill in the art. Other similar substitutions can be made between the different embodiments.

Thus, it will be appreciated by persons skilled in the art that various deviations from the described embodiments of the invention are possible and that many modifications and improvements may be made within the scope and spirit thereof. It will be understood that the invention is not limited by the specific embodiments described herein, but only by scope of the appended claims.

What is claimed is:

1. A support post for use with a dental implant, said dental implant having an internally threaded bore therein and a boss located on a gingival end, said implant being substantially located below an exterior surface of the gingiva and contacting a jawbone, said support post comprising:

a ceramic portion adapted to support a prosthesis thereon, said ceramic portion having a supragingival end for protruding beyond said gingiva and a subgingival end for extending into said gingiva, said ceramic portion having a passageway extending therethrough;

a screw for removably engaging the threads of said internally threaded bore in said implant and inserted through said passageway, said screw comprising a head and a threaded section; and a metal portion comprising a lower section and an upper section extending into said passageway, said metal portion abutting said subgingival end of said ceramic portion, said lower section adapted to receive and engage said corresponding boss of said dental implant, said metal portion having an opening to provide access of said screw, said upper section having an uppermost surface remaining entirely below said head of said screw, said screw head engaging at least the metal portion for mounting said metal and ceramic portions onto said implant.

2. The support post of claim 1, wherein said uppermost surface of said upper section defines a shoulder for engaging said head of said screw.

3. The support post of claim 1, wherein said passageway of said ceramic portion narrows to define a shoulder for engaging said head of said screw.

4. The support post of claim 1, wherein said uppermost surface of said upper section defines a first shoulder and said passageway of said ceramic portion narrows to define a second shoulder, said first and said second shoulders adapted to engage said head of said screw.

5. The support post of claim 1, wherein said metal portion is made of titanium or titanium alloy.

6. The support post of claim 1, wherein the hardness of the material used in forming said metal portion is not greater than the hardness of the material used in forming said dental implant.

7. The support post of claim 1, wherein said metal portion and said dental implant are made from the same material.

8. The support post of claim 1, wherein said lower section of said metal portion comprises a flange and a polygonal section.

9. The support post of claim 8, wherein said flange has an exterior surface, said exterior surface tapering inwardly toward said dental implant.

10. The support post of claim 9, wherein said subgingival end of said ceramic portion has an outer surface generally following a contour of said exterior surface of said flange.

11. The support post of claim 1, wherein said upper section of said metal portion is generally tubular.

12. A post for mounting on a dental implant having a non-round fitting, said implant being located in a jawbone with said non-round fitting exposed through gingiva overlying said jawbone, said post comprising:

a metallic portion having a lower section and an upper section, said lower section having a flange, a lowermost surface for engaging said implant, and a fitting for mating with said non-round fitting of said implant, said upper section extending above said lower section;

a ceramic portion attached to said metallic portion, said ceramic portion having a bottom section for engaging said flange and a generally tubular top section surrounding said upper section of said metallic portion and extending thereabove; and a screw for retaining said lowermost surface of said metallic portion against said implant, said screw for removably engaging said implant and having a head residing within said generally tubular top section of said ceramic portion and entirely above said upper section of said metallic portion, said screw head engaging at least the metallic portion for mounting said metallic and ceramic portions onto said implant.

13. The post of claim 12, wherein said upper section of said metallic portion defines a shoulder for engaging said head of said screw.

14. The post of claim 13, wherein said head of said screw further engages a surface of said ceramic portion.

15. The post of claim 12, wherein said metallic portion is made of titanium or titanium alloy.

16. The post of claim 12, wherein the hardness of the material used in forming said metallic portion is not greater than the hardness of the material used in forming said dental implant.

17. The post of claim 12, wherein said metallic portion and said dental implant are made from the same material.

18. The post of claim 12, wherein said fitting of said metallic portion is adapted to mate with a hexagon.

19. The post of claim 12, wherein said flange has an exterior surface, said exterior surface tapering inwardly toward said implant.

20. The post of claim 19, wherein an end of said bottom section of said ceramic portion has an outer surface generally following a contour of said exterior surface of said flange.

21. The post of claim 12, wherein said upper section of said metallic portion is generally tubular.

22. A support post for use with a dental implant, said dental implant having an internally threaded bore and a boss located on a gingival end, said implant being substantially located below an exterior surface of the gingiva and contacting a jawbone, said support post comprising:

a ceramic portion adapted to support a prosthesis thereon, said ceramic portion having a supragingival end for protruding beyond said gingiva and a subgingival end for extending into said gingiva, said ceramic portion having a passageway extending therethrough;

a screw for removably engaging the threads of said internally threaded bore in said implant and inserted through said passageway, said screw comprising a head and a threaded section, said head having a top most surface; and a metal portion comprising a lower section and an upper section, said metal portion abutting said subgingival end of said ceramic portion, said lower section adapted to receive and engage said corresponding boss of said dental implant, said metal portion having an opening to provide access of said screw, said upper section extending at least partially into said passageway and having an uppermost surface below said supragingival end of said ceramic portion and near said top most surface of said head of said screw.

23. The support post of claim 22, wherein said uppermost surface of said upper section defines a shoulder for engaging said head of said screw.

24. The support post of claim 22, wherein said metal portion is made of titanium or titanium alloy.

25. The support post of claim 22, wherein the hardness of the material used in forming said metal portion is not greater than the hardness of the material used in forming said dental implant.

26. The support post of claim 22, wherein said metal portion and said dental implant are made from the same material.

27. The support post of claim 22, wherein said lower section of said metal portion comprises a flange and a polygonal section.

28. The support post of claim 27, wherein said flange has an exterior surface, said exterior surface tapering inwardly toward said dental implant.

29. The support post of claim 28, wherein said subgingival end of said ceramic portion has an outer surface generally following a contour of said exterior surface of said flange.

30. The support post of claim 22, wherein said upper section of said metal portion is generally tubular.

* * * * *